United States Patent [19]

Sakakibara et al.

[11] Patent Number: 4,482,707
[45] Date of Patent: Nov. 13, 1984

[54] AMINOGLYCOSIDE ANTIBIOTIC SACCHAROCINS

[75] Inventors: Hideo Sakakibara; Shuzo Satoi; Masashi Awata; Hitoshi Sagai; Mitsuo Hayashi; Naoki Muto; Masaki Takada, all of Shizuoka, Japan

[73] Assignee: Toyo Jozo Kabushiki Kaisha, Shizuoka, Japan

[21] Appl. No.: 447,967

[22] Filed: Dec. 8, 1982

[30] Foreign Application Priority Data

Dec. 8, 1981 [JP] Japan .................... 56-197953
Jun. 16, 1982 [JP] Japan .................... 57-104177

[51] Int. Cl.³ .................... C07H 15/22; C12P 19/44
[52] U.S. Cl. .................... 536/16.8; 424/181; 435/74; 536/18.1
[58] Field of Search .................... 536/16.8, 18.1

[56] References Cited

U.S. PATENT DOCUMENTS 4,358,585 11/1982 Igarashi et al. .................... 536/16.8
4,360,665 11/1982 Kirst .................... 536/16.8

Primary Examiner—Johnnie R. Brown
Attorney, Agent, or Firm—Young & Thompson

[57] ABSTRACT

Antibiotic saccharocins of the formula

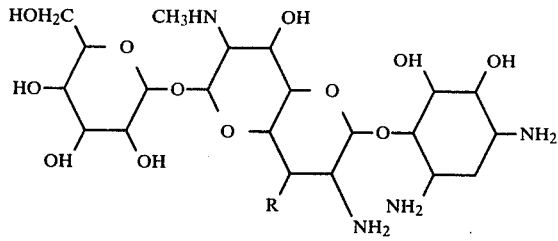

wherein R is hydrogen (saccharocin) or hydroxyl (3'-oxysaccharocin) are produced by culturing a microorganism belonging to the genus Saccharopolyspora, for example Saccharopolyspora sp. AC 3440 FERM-P No. 6238, in a conventional nutrient medium, and separating the thus-produced saccharocins from the cultured medium. The noval saccharocins exhibit anti-bacterial activity against Gram negative bacteria.

1 Claim, 4 Drawing Figures

AMINOGLYCOSIDE ANTIBIOTIC SACCHAROCINS

This invention relates to novel aminoglycoside antibiotic saccharocins.

The antibiotic saccharocins are represented by the formula

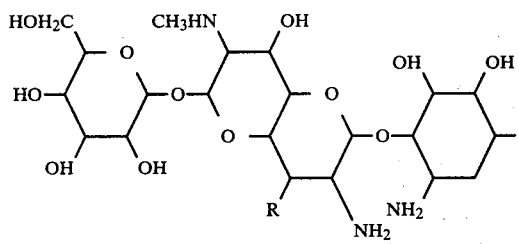

wherein R is hydrogen or hydroxyl. In this invention, such an antibiotic wherein R is hydrogen is designated saccharocin and the antibiotic wherein R is hydroxyl is designated 3'-oxysaccharocin. However, both of these antibiotics are generally designated saccharocins.

The above antibiotic saccharocins can be produced by culturing an antibiotic saccharocin and/or 3'-oxysaccharocin producing microorganism belonging to the genus Saccharopolyspora, for example Saccharopolyspora sp. AC 3440 FERM-P No. 6238, in a nutrient medium, and separating the thus-produced saccharocins from the cultured medium.

IN THE ACCOMPANYING DRAWINGS

Figure 1:
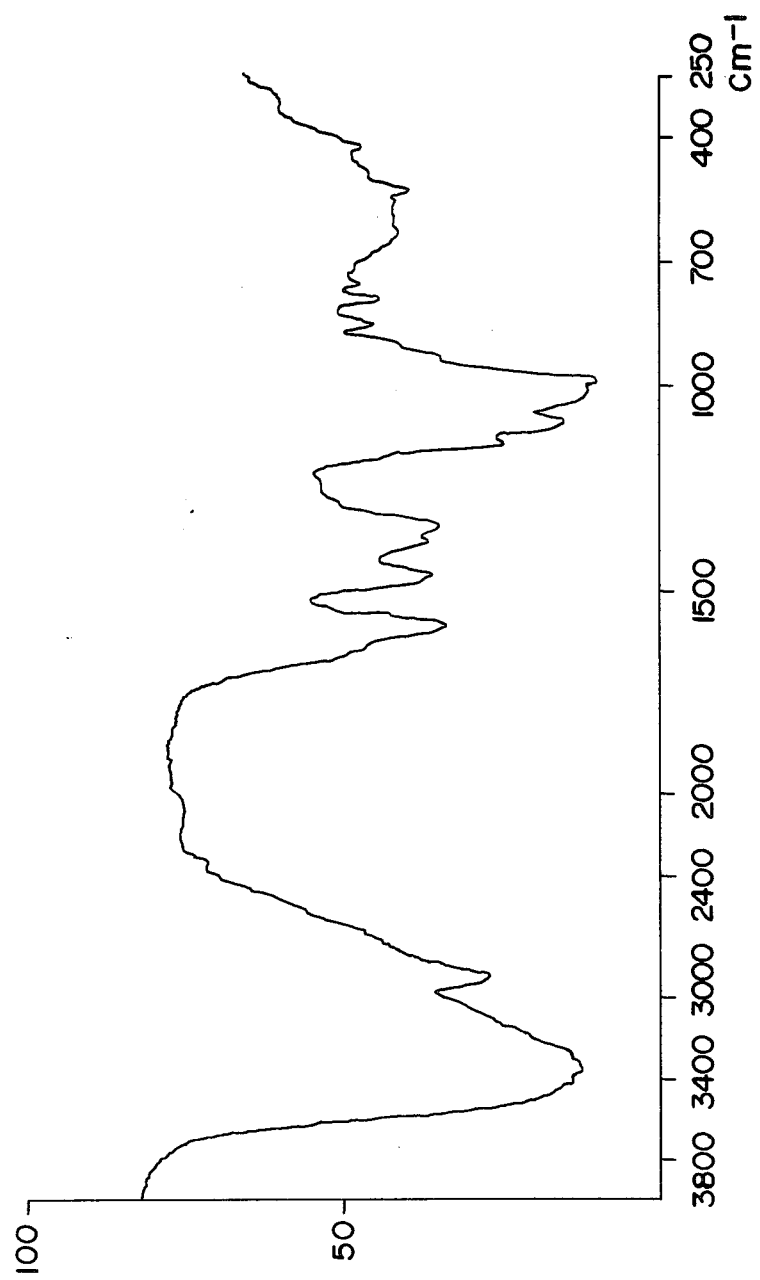
Figure 2:
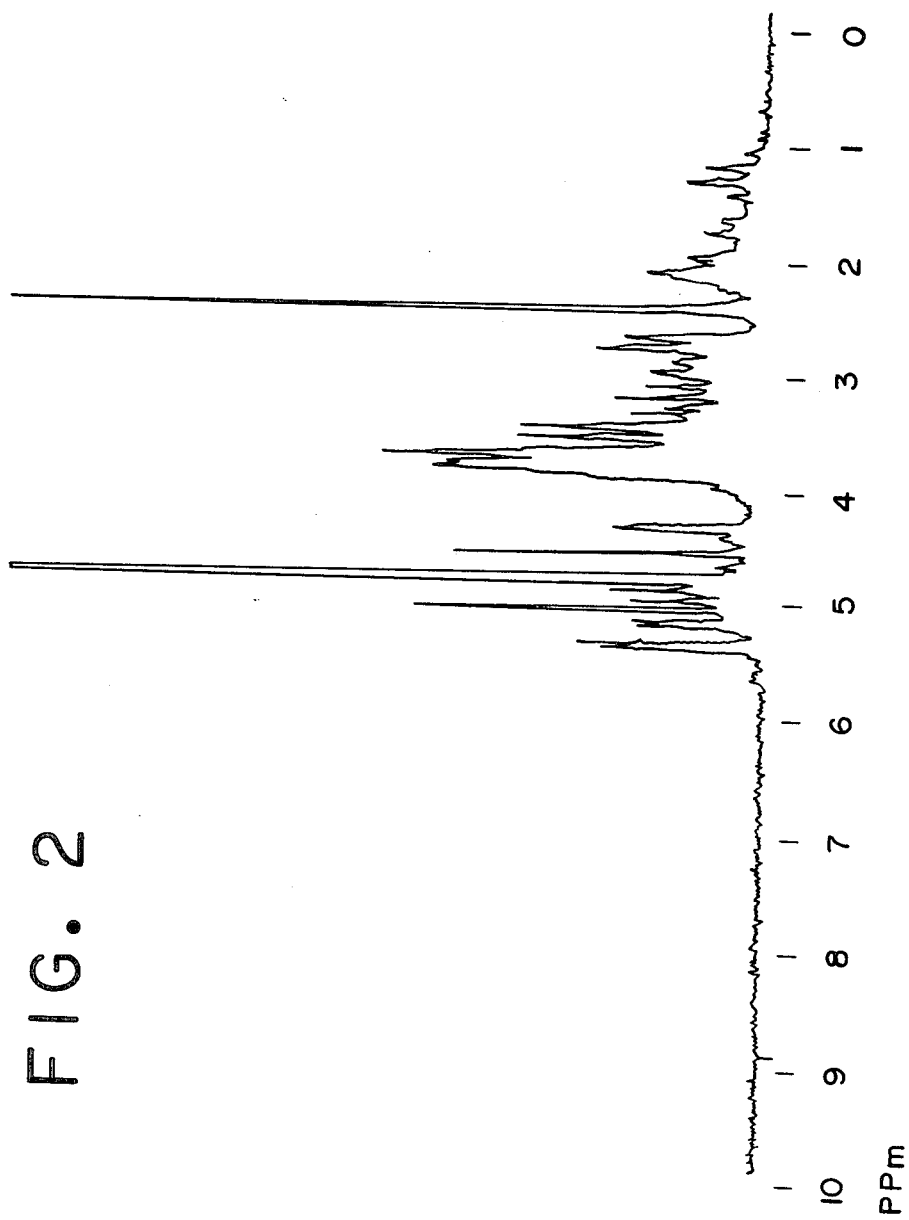
Figure 3:
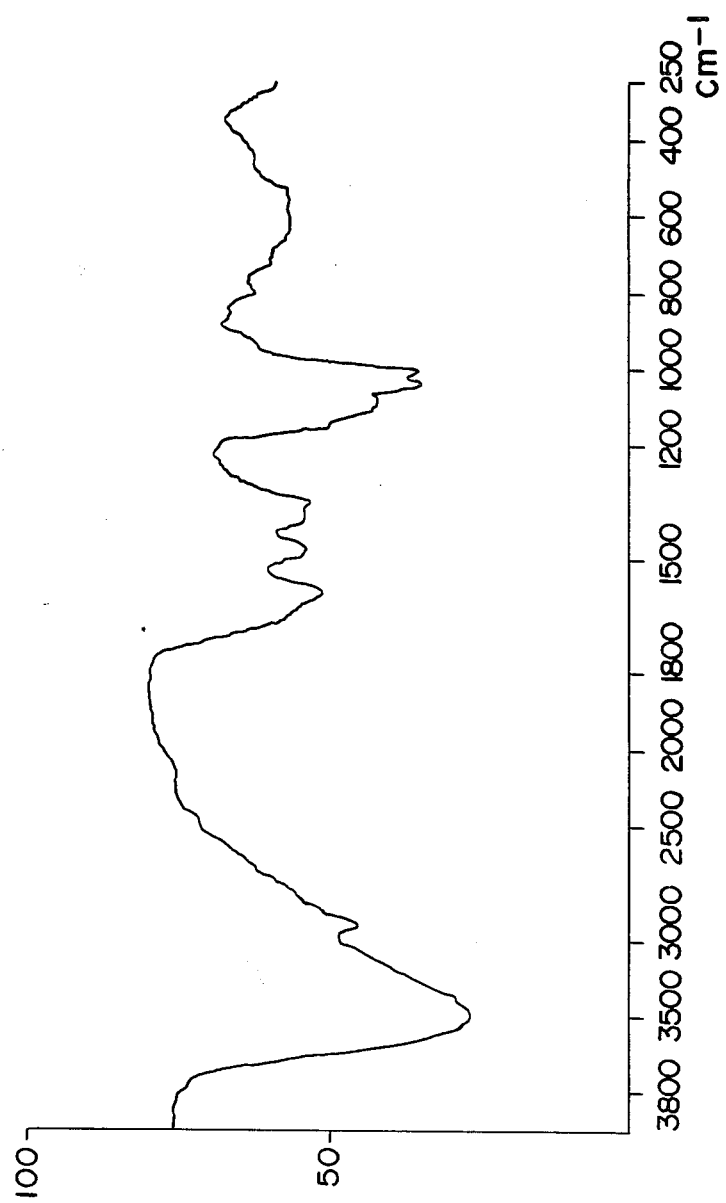
Figure 4:
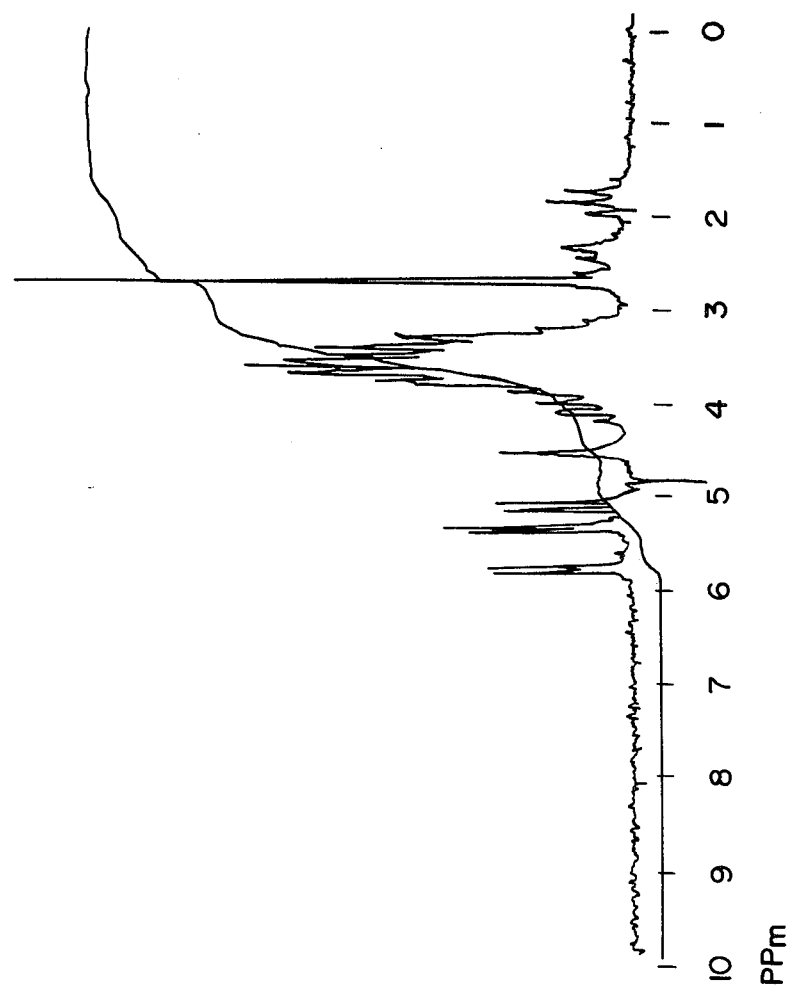

FIG. 1 is the IR spectrum of saccharocin.
FIG. 2 is the NMR spectrum of saccharocin.
FIG. 3 is the IR spectrum of 3'-oxysaccharocin; and
FIG. 4 is the $^1$H-NMR spectrum of 3'-oxysaccharocin.

The physico-chemical properties of antibiotic saccharocins are as follows:

|  | Saccharocin | 3'-oxysaccharocin |
|---|---|---|
| M.P. | 188–190° C. (decomp.) | over 230° C. (decomp.) |
| Optical rotation: | $[\alpha]_D^{24} + 163.5°$ | $[\alpha]_D^{24} + 162°$ |
|  | (c = 1.0, H$_2$O) | (c = 0.25, H$_2$O) |
| Elementary analysis: | [C$_{21}$H$_{40}$N$_4$O$_{12}$.2H$_2$O] | [C$_{21}$H$_{40}$N$_4$O$_{13}$.2H$_2$O] |
|  | C %　　H %　　N % | C %　　H %　　N % |
| Calculated: | 43.74　　7.69　　9.72 | 42.56　　7.48　　9.45 |
| Found: | 43.35　　7.46　　9.74 | 42.07　　7.12　　9.03 |
| Molecular weight: (field desorption mass spectrum) | 540 | 556 |
| UV-spectrum: | end-absorption between 220–360 nm in H$_2$O | end-absorption between 220–360 nm in H$_2$O |
| IR-spectrum: (KBr tablet) | FIG. 1 absorption band at 3350, 2900, 1585, 1460, 1380, 1140, 1090, 990 cm$^{-1}$. | FIG. 3 absorption band at 3350, 2900, 1585, 1460, 1390, 1345, 1040, 1000 cm$^{-1}$. |
| $^1$H—NMR (D$_2$O, 100 MHz, inner standard DSS): | FIG. 2 | FIG. 4 |
| $^{13}$C—NMR: | No.　　ppm | No.　　ppm |
|  | 1　　101.4 | 1　　102.6 |
|  | 2　　96.5 | 2　　97.0 |
|  | 3　　95.1 | 3　　95.9 |
|  | 4　　87.6 | 4　　88.4 |
|  | 5　　78.1 | 5　　78.4 |
|  | 6　　76.7 | 6　　76.9 |
|  | 7　　73.5 | 7　　74.5 |
|  | 8　　73.4 | 8　　74.1 |
|  | 9　　71.4 | 9　　73.8 |
|  | 10　　71.0 | 10　　72.4 |
|  | 11　　70.2 | 11　　72.0 |
|  | 12　　67.9 | 12　　71.1 |
|  | 13　　67.4 (dioxane) | 13　　70.4 |
|  | 14　　66.4 | 14　　67.4 (dioxane) |
|  | 15　　62.3 | 15　　66.6 |
|  | 16　　61.3 | 16　　62.3 |
|  | 17　　51.1 | 17　　61.8 |
|  | 18　　50.2 | 18　　56.7 |
|  | 19　　49.8 | 19　　51.3 |
|  | 20　　36.3 | 20　　50.1 |
|  | 21　　33.0 | 21　　36.8 |
|  | 22　　32.7 | 22　　33.2 |
| Color reaction: |  |  |
| ninhydrin: | positive | positive |
| decoloration of KMnO$_4$: | positive | positive |
| Elson-Morgan: | negative | negative |
| Sakaguchi: | Negative | negative |
| Color: | white powder | white powder |
| Nature: | basic | basic |
| Thin Layer Chromatography: |  |  |
| carrier: silica-gel, Merck Art. 5735; |  |  |
| developer: chloroform-methanol-28% aq. ammonia (2:3:2) |  |  |
|  | Rf = 0.32 | Rf = 0.24 |
| developer: chloroform-methanol-14% aq. ammonia (1:2:1) |  |  |
|  | Rf = 0.26 | Rf = 0.17 |

|  | Saccharocin | 3'-oxysaccharocin |
|---|---|---|
| Solubility: | | |
| soluble: | water | water |
| insoluble: | acetone, benzene, ethyl acetate | acetone, benzene, ethyl acetate |

According to the above physico-chemical properties, saccharocin and 3'-oxysaccharocin have never been found in the prior published data, and hence are apparently novel antibiotics and so are designated saccharocin and 3'-oxysaccharocin.

The minimum inhibitory concentration (MIC) of saccharocin and 3'-oxysaccharocin by the agar dilution method are shown in Table 1.

TABLE 1

| Test Organisms | Saccharocin MIC (mcg/ml) | 3'-oxy-saccharocin MIC (mcg/ml) |
|---|---|---|
| Staphylococcus aureus ATCC 6538P | 12.5 | 25 |
| Staphylococcus aureus MS27 | 12.5 | 25 |
| Staphylococcus aureus 0119 | 6.3 | 12.5 |
| Staphylococcus epidermidis ap-al-1 | 6.3 | 12.5 |
| Streptococcus pyogenes N.Y.5 | 25 | 50 |
| Bacillus subtilis ATCC6633 | 0.8 | 3.1 |
| Escherichia coli NIHJ-JC2 | 6.3 | 12.5 |
| Escherichia coli W3630 | 1.6 | 3.1 |
| Escherichia coli W3630RGN14 | 3.1 | 12.5 |
| Citrobacter freundie GN346 | 6.3 | 12.5 |
| Klebsiella pneumoniae ATCC 10031 | 3.1 | 12.5 |
| Salmonella enteritidis gaertner | 6.3 | 12.5 |
| Shigella sonnei E33 | 6.3 | 25 |
| Proteus morganii 0239 | 6.3 | 12.5 |
| Proteus rettgeri ACR | 3.1 | 12.5 |
| Enterobacter aerogenes 055 | 6.3 | 12.5 |
| Enterobacter cloacae GN336 | 6.3 | 12.6 |
| Serratia marcescens | 6.3 | 12.5 |
| Pseudomonas aeruginosa | 25 | 50 |
| Pseudomonas aeruginosa ML4561 | 25 | 50 |
| Pseudomonas aeruginosa ML4561 Rm3166 | 12.5 | 25 |
| Pseudomonas aeruginosa ML4561 Rm3164-1 | 25 | 50 |
| Pseudomonas aeruginosa ML4561 RP4 | 12.5 | 50 |
| Pseudomonas aeruginosa 1946 | >100 | >50 |
| Pseudomonas aeruginosa 2512 | 50 | 50 |
| Pseudomonas putida 1842 | 25 | 50 |
| Pseudomonas martfiriae 1850 | >100 | >50 |

As shown in Table 1, the novel saccharocins exhibit antibacterial activity against Gram negative bacteria.

The saccharocins can be prescribed in the form of non-toxic physiologically acceptable acid addition salts such as salts of inorganic or organic acids, for example, hydrochloride, iodide, sulfate, phosphate, carbonate, acetate, fumarate, malate, citrate, mandelate, succinate, ascorbate, aspartate or glutamate. Saccharocins or non-toxic salts thereof can be prepared in the form of an injectable preparation of 20–100 mg/vial or 20–100 mg/ampule, or 20–100 mg/suppository. These saccharocins or the pharmaceutically acceptable acid addition salts thereof can also be used for poultry, livestock or fish or feed additives. Although the novel saccharocins can easily be dissolved in water, they can also be prepared in the form of acid addition salts for treatment or growth stimulants for animals.

The saccharocin and/or 3'-oxysaccharocin producing microorganism, an Actinomycetes strain AC 3440, was isolated from a soil sample collected in a field at Ato-cho, Ato-gun, Yamaguchi-ken, Japan, and was identified as belonging to genus Saccharopolyspora. This strain was referred to as Saccharopolyspora sp. AC 3440, and was deposited in the Fermentation Research Institute, Agency of Industrial Science and Technology, MITI, Japan, under deposit number FERM-P No. 6238.

The taxonomic properties of this microorganism are as follows:

I. Morphological properties:

Upon starch-inorganic agar medium [ISP medium 4, Int. J. System. Bacteriol., 16, 313–340 (1966)], at 37° C. for 10–14 days culture, the following characteristics were observed.

Substrate mycelia are wavy or straight, branched growth, splitting for part of the mycelia or upon later cultivation, and of a diameter 0.4–0.6μ. No spore formation.

Aerial mycelia grown from substrate mycelia are wavy or straight, single branching, diameter 0.5–0.7μ, with loops or 2–3 weakly rounded spiral or wavy or straight at the cusp.

Bead-like chains of more than 10 spores branched from aerial mycelia are formed, and often the parts between the spores are separated by empty mycelia.

The spores are elliptical or short cylindrical, 0.5–0.7×0.7–1.3μ, and covered by a spore coat with many tufty straight or wavy long hairy substances.

No formation of sporangia, sclerotia or flagella spores on the substrate mycelia or serial mycelia was noted.

II. Grams strain: positive, Acid-fast stain: negative.

III. Mycelial composition:

(1) Meso-type diaminopimelic acid (DAP) analyzed by the method according to B. Becker, et al. [Appl. Microbiol., 12, 421–423 (1964)] was detected.

Arabinose and galactose analyzed by the method according to Lechevalier [J. Lab. Clin. Med., 71, 934–944 (1968)] were detected.

(2) Lipids analysis according to H. Mordarska et al. [J. Gen. Microb., 71, 77–86 (1972)]: no lipid LCN-A was found; and by method according to D. E. Minnikin et al. [J. Gen. Microbiol., 88, 200–204 (1975)]: no nocardomycolic acid and mycolic acid were found.

IV. Cultural characteristics:

Observations on various media cultured at 37° C. for 14 days are shown in Table 2. Color indication is made according to the Color Harmony Manual, 4th Ed., 1958 (Container Corp. of America).

V. Physiological properties:

The culture was observed at 37° C. for 14 days except where specifically indicated.

(1) Growth temperature: 22°–53° C. (optimum growth temperature: 30–45PC) [ISP medium 2]
(2) Gelatin liquefaction: positive
(3) Starch hydrolysis: positive
(4) Skim milk: peptonization-positive; coagulation-negative
(5) Melanin-like pigment formation: negative (ISP media 7 and 6)
(6) Nature: aerobic
(7) H$_2$S formation: positive [lead acetate containing paper, ISP medium 6]

(8) Nitrate reduction: negative [J. Bacteriol., 73, 15–27 (1957)]
(9) Resistance to lysozyme: non-resistant [J. Gen. Microbiol., 45, 355–364 (1961)]
(10) Resistance to sodium chloride: growth—0–10% no growth: over 11%
(11) Resistance on antibiotics: [J. Antibiot., 32, 180–186 (1979)]

| Antibiotic | MIC (mcg/ml) |
|---|---|
| Kanamycin | >100 |
| Gentamicin | >100 |
| Paromomycin | 50 |
| Streptomycin | 25 |
| Neomycin | 100 |
| Tobramycin | >100 |
| Rifampicin | <12.5 |
| Leucomycin $A_5$ | >100 |

(12) Decomposition of various substance:

| | | | |
|---|---|---|---|
| tyrosine | + | adenine | + |
| casein | + | esculin | + |
| xanthin | + | kelatin | − |
| hypoxanthin | + | xylan | − |
| cellulose | − | elastin | + |

(+: positive, −: negative)

[T. R. G. Gray et al. ed. "Ecology of Soil Bacteria", 293–321, Liverspool Univ. Press, Liverpool (1967), J. Gen. Microbiol., 69, 33–80 (1971) and J. Gen. Microbiol., 88, 75–85 (1975)]

(13) Utilization of carbon sources:

| (a) sugars: | | | |
|---|---|---|---|
| L-arabinose | ± | D-ribose | + |
| D-fructose | + | trehalose | + |
| D-galactose | + | sucrose | + |
| D-glucose | + | L-sorbose | ± |
| glycerol | + | D-sorbitol | + |
| i-inositol | + | dulcitol | − |
| D-mannose | + | xylose | + |
| D-mannitol | + | salicine | + |
| melezitose | − | cellobiose | + |

| -continued | | | |
|---|---|---|---|
| melibiose | − | starch | + |
| β-lactose | + | adnitol | + |
| maltose | + | erythritol | + |
| raffinose | + | α-D-methylglycoside | + |
| L-rhamnose | + | | |
| (b) organic acids: | | | |
| sodium acetate | + | sodium propionate | + |
| sodium benzoate | − | sodium pyruvate | + |
| sodium butyrate | + | sodium succinate | + |
| sodium citrate | + | sodium tartrate | + |
| sodium fumarate | + | sodium adipate | + |
| sodium malate | + | sodium sebacate | + |

(ISP medium 9, +: positive, ±: doubtful, −: negative)
[according to J. Bacteriol., 73, 15–27 (1957)]

As shown in the above, the characteristics of the strain AC 3440 are: (1) by morphological observation: aerial mycelia grown from splitting substrate mycelia, together with forming loosely round spiral and straight

TABLE 2

| Medium | Growth | Color of substrate mycelia | Aerial mycelia | Soluble pigment |
|---|---|---|---|---|
| Sucrose-nitrate agar (Waksman medium No. 1)[1] | good | amber (3pe)–mustard gold (2pe) | no good or trace, white (a) | amber (3pe)–mustard gold (2pe) |
| Glucose-asparagine agar (Waksman medium No. 2) | moderate | light ivory (2ca)–colorless | few: white (a) | none |
| Gycerol-asparagine agar (ISP medium 5)[2] | moderate–good | light wheat (2ea)–maize (2hb) | no good or moderate: white (a) | amber (3pe) few |
| Starch-inorganic salt agar (ISP medium 4) | good | amber (3pe)–mustard gold (2pe) | no good or moderate white (a) | none |
| Tyrosine agar (ISP medium 7) | good | amber (3pe)–mustard gold (2pe) | moderate: white (a) | none |
| Oatmeal agar (ISP medium 3) | good | light ivory (2ca)–colorless | none | none |
| Yeast extract-malt extract agar (ISP medium 2) | good | mustard gold (2pe)–amber (3pe) | few: white (a) | gold (21c) |
| Nutrient agar (Waksman medium No. 4) | moderate | light ivory (2ca)–colorless | few or none white (a) | none |
| Glycerol-nitrate agar (Waksman medium No. 1) | good | maize (2hb) | moderate: white (a) | gold (21c) few |
| Benett's agar (Waksman medium No. 30) | good | mustard gold (2pe)–bright gold (2pc) | few: white (a) | none |
| Emason agar (Waksman medium No. 28) | good | amber (3pe)–mustard gold (2pe) | few: white | amber (3pe) or mustard gold (2pe) |
| Hickey-Tresner's agar (Waksman medium No. 32) | good | mustard gold (2pe) | few: white (a) | none |

[1]Waskman, S.A., "The Actinomycetes" Vol. 2, 1961, p. 327–334.
[2]Inter. J. System. Bacteriol., 16, 313–340 (1966).

or wavy spore chains, and spores covered with a long tufty spore coat; (2) by cell-wall analysis: detecting meso-diaminopimelic acid, arabinose and galactose, but not detecting lipids LCN-A, nocardomycolic acid and mycolic acid; (3) by staining: Gram positive and acid-fast stain negative, and (4) aerobic nature.

Referring to the above taxonomic properties, the strain AC 3440 was almost identical with the characteristics of genus Saccharopolyspora Lacey Goodfellow [J. Gen. Microbiol., 88, 75–85 (1975)]. This strain is accordingly referred to as Saccharopolyspora sp. AC 3440.

The strain which can be used in the present invention is, for example, Saccharopolyspora sp. AC 3440 FERM-P No. 6238. The invention is not limited to this strain, however, as other saccharocin and/or 3'-oxysaccharocin producing strains belonging to the above genus and natural or artificial mutants thereof can be used in the present invention.

In an embodiment of the present invention, the above saccharocins producing microorganisms belonging to genus Saccharopolyspora are aerobically cultured in a conventional medium. The cultivation of the microorganisms can be carried out by liquid or solid culture.

Submerged aeration culture is preferably for industrial production.

A conventional culture medium for microorganisms can preferably be used. As for the carbon sources, assimilable carbon sources such as glucose, sucrose, dextrin, starch or molasses can be used. Assimilable nitrogen sources such as corn steep liquor, soybean powder, cotton seed powder, peptone, meat extract, yeat extract, ammonium or nitrate salt can be used. Various salts such as sodium chloride, potassium chloride, potassium phosphate or magnesium sulfate are optionally used.

The culturing temperature can be selected within the ranges for the growth of microorganisms and the production of saccharocins, and is preferably 25°–35° C. The culturing time can be selected depending on conditions and is usually 72–140 hours. Culturing should naturally be terminated when saccharocins production is substantially complete.

The saccharocins are formed in the cultured liquid.

Isolation of the antibiotics from the cultured broth can be carried out according to the nature of basic aminoglycoside saccharocins.

The produced saccharocins can be detected by the conventional agar plate method using *Bacillus subtilis* ATCC 6633 as the test organism.

An embodiment of the isolation of saccharocins from cultured broth is as follows:

Saccharocin and/or 3'-oxysaccharocin producing microorganisms are cultured and the cultured broth is filtered. The cultured broth is adjusted to acidic pH because of the aminoglycoside nature of the saccharocins, and is neutralized and filtered to obtain a culture filtrate. The active principles are adsorbed on an ion-exchange resin such as Amberlite IRC-50 ($NH_4^+$ type) (trademark) after passing the culture filtrate through a column of the same. The active principles are eluted by 1N aqueous ammonia, and the eluate is concentrated. After adjusting the pH, the concentrate is passed through a column of CM-Sephadex C-25 ($NH_4^+$ type) to adsorb the active principles, and the column eluted with 0.03N aqueous ammonia, whereby at first 3'-oxysaccharocin and later saccharocin are eluted, The eluates are concentrated and lyophilizated to obtain saccharocin and 3'-oxysaccharocin as the purified white free base. The thus-obtained products show a single spot upon thin layer chromatography.

The following examples illustrate the present invention but are not to be construed as limiting:

EXAMPLE 1

An aqueous medium (100 ml, pH 7.0) comprising dextrin 1%, glucose 1%, casein hydrolyzate 0.5%, yeast extract 0.5% and calcium carbonate 0.1% (percentages are W/V) in a 500 ml Erlenmeyer flask was sterilized at 120° C. for 20 minutes. Saccharopolyspora sp. AC 3440 FERM-P No. 6238 was inoculated therein and the mixture was shake cultured at 30° C. for 72 hours to prepare a seed culture.

A main culture medium (100 ml, pH 7.0) comprising glucose 0.2%, glycerol 4%, peptone 5%, starch 0.2%, defatted soybean powder 0.5%, dry yeast 0.5%, NaCl 0.5% and calcium carbonate 0.2% in a 500 ml Erlenmeyer flask was sterilized. One hundred flasks of the main culture medium were inoculated each with 3% of the above seed culture, and shake cultured at 30° C. for 96 hours. The cultured masses were combined to obtain a cultured broth (10 lit.).

EXAMPLE 2

Cultured broth obtained in Example 1 was adjusted to pH 2.0 by adding 12N $H_2SO_4$, the mixture was stirred for 10 minutes and further adjusted to pH 7.0 by adding conc. aqueous ammonia, and centrifuged to obtain a supernatant solution (9 lit.). The supernatant solution was charged on a column of Amberlite IRC-50 ($NH_4^+$ type, 1 lit.) (Rohm Haas Co.), washed with water, and eluted with 1N-aqueous ammonia (2 lit.) The eluate was concentrated in vacuo to 30 ml. The concentrate was adjusted to pH 7.0 by adding 6N-$H_2SO_4$, charged on a column (diameter 3 cm) of CM-Sephadex C-25 ($NH_4^+$ type, 300 ml, Pharmacia Fine Chem. Co.) and eluted with 0.03N aqueous ammonia.

The eluates were fractionated into fractions of 20 ml each. Each fraction was checked by thin layer chromatography developed by chloroform-methanol-conc. aq. ammonia (2:3:2) with ninhydrin coloration. Fractions Nos. 98–109 contained 3'-oxysaccharocin and fractions Nos. 124–143 contained saccharocin. Each fraction was collected, concentrated in vacuo, and lyophilized to obtain a white powder. The powder was dried in vacuo over phosphorous pentoxide at 40° C. for 48 hours to obtain purified crystalline white powder saccharocin free base (110 mg) and 3'-oxysaccharocin free base (30 mg).

What is claimed is:

1. An antibiotic saccharocin of the formula

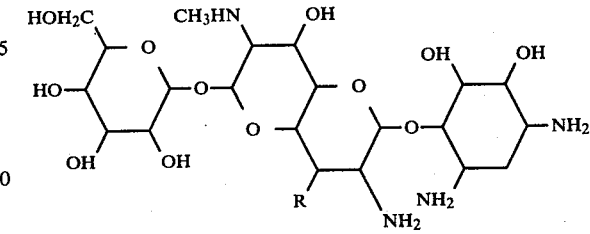

wherein R is hydrogen or hydroxyl, or a pharmaceutically acceptable acid addition salt thereof.

* * * * *